United States Patent [19]

Hirai et al.

[11] Patent Number: 4,747,855

[45] Date of Patent: May 31, 1988

[54] SOLID ABSORBENT FOR UNSATURATED HYDROCARBON AND PROCESS FOR SEPARATION OF UNSATURATED HYDROCARBON FROM GAS MIXTURE

[75] Inventors: Hidefumi Hirai, 14-10, Yutenji 1-chome, Meguro-ku, Tokyo, Japan; Makoto Komiyama, Tokyo; Keiichiro Wada, Kiyose, both of Japan

[73] Assignee: Hidefumi Hirai, Tokyo, Japan

[21] Appl. No.: 6,343

[22] Filed: Jan. 21, 1987

Related U.S. Application Data

[63] Continuation of Ser. No. 829,867, Feb. 18, 1986, abandoned, which is a continuation of Ser. No. 602,743, Apr. 23, 1984, abandoned.

[30] Foreign Application Priority Data

Jul. 20, 1983 [JP] Japan ............... 58-132360
Jan. 7, 1984 [JP] Japan ............... 59-001164

[51] Int. Cl.$^4$ ............................................. B01D 53/04
[52] U.S. Cl. ............................. 55/74; 55/387; 585/829; 585/849
[58] Field of Search ............... 55/63, 74, 387; 502/417, 438; 585/829, 846, 848, 849

[56] References Cited

U.S. PATENT DOCUMENTS

| | | | |
|---|---|---|---|
| 1,519,470 | 2/1924 | Wilson et al. | 502/417 |
| 2,476,472 | 7/1949 | Arnold et al. | 585/829 X |
| 2,528,517 | 11/1950 | Hormats | 502/417 |
| 2,606,938 | 8/1952 | Robinson | 585/829 X |
| 2,920,050 | 1/1960 | Blacet et al. | 55/74 X |
| 2,963,441 | 12/1960 | Dolian et al. | 55/74 X |
| 3,276,186 | 10/1966 | Hronas et al. | 55/74 X |
| 3,416,293 | 12/1968 | Alexander | 55/74 X |
| 3,651,159 | 3/1972 | Long et al. | 55/74 X |
| 3,883,637 | 5/1975 | Benedict | 55/74 X |
| 4,234,460 | 11/1980 | Nishimura et al. | 502/417 |
| 4,242,226 | 12/1980 | Siren | 55/74 X |
| 4,470,829 | 9/1984 | Hirai et al. | 55/74 X |

FOREIGN PATENT DOCUMENTS 2840791 4/1979 Fed. Rep. of Germany .......... 55/74
3013256 10/1981 Fed. Rep. of Germany ...... 502/417

*Primary Examiner*—Robert Spitzer
*Attorney, Agent, or Firm*—Cushman, Darby & Cushman

[57] ABSTRACT

A solid adsorbent for an unsaturated hydrocarbon including (a) (i) a copper(I) halide or oxide or (ii) a halide, carboxylate, sulfate, basic salt, oxide, or amine complex salt of copper(II) and (b) activated carbon or graphite is described.

This solid adsorbent can effectively adsorb an unsaturated hydrocarbon such as ethylene from a gas mixture by being placed in contact with the gas mixture at a temperature of $-40°$ C. to $90°$ C. under normal pressure.

7 Claims, No Drawings

SOLID ABSORBENT FOR UNSATURATED HYDROCARBON AND PROCESS FOR SEPARATION OF UNSATURATED HYDROCARBON FROM GAS MIXTURE

This is a continuation of application Ser. No. 829,867, filed Feb. 18, 1986, which was abandoned upon the filing hereof and which was a continuation of application Ser. No. 602,743 filed Apr. 23, 1984, now abandoned.

BACKGROUND OF THE INVENTION

1. Field of the Invention

The present invention relates to a solid adsorbent for an unsaturated hydrocarbon such as ethylene and propylene. The present invention also relates to a process for separating an unsaturated hydrocarbon from a gas mixture containing the same, together with nitrogen, oxygen, methane, ethane, carbon dioxide, and hydrogen.

2. Description of the Prior Art

Unsaturated hydrocarbons such as olefins and dienes are the most important basic or fundamental raw materials in the chemical industry. These unsaturated hydrocarbons are produced by the pyrolysis of saturated hydrocarbons such as natural gases, refinery gases, and petroleum fractions. Furthermore, substantial amounts of unsaturated hydrocarbons are contained in off gases derived, as by-products, from fluid catalytic cracking and also in purge gases derived from various processes. These gases, however, contain unsaturated hydrocarbons together with nitrogen, oxygen, methane, ethane, carbon dioxide, and hydrogen. Furthermore, these gases contain 1000 to 20000 ppm of water. Accordingly, the unsaturated hydrocarbons must be separated from these gas mixtures in order to use the unsaturated hydrocarbons as raw materials for chemical synthesis.

Known processes for separating unsaturated hydrocarbons from gas mixtures include a so-called cryogenic gas separation process. In this process, a gas mixture is liquefied by cooling and is then fractionated at an extremely low temperature. However, this process also has disadvantages in that complicated refrigeration and heat recovery systems are required, the equipment is expensive due to the use of high-grade materials, and the power consumption is large. In addition, water and carbon dioxide contained in the gas mixture must be removed from the gas mixture in a pre-treatment apparatus so that the content thereof is less than 1 ppm, since clogging will occur in a low-temperature pipe line system when water and carbon dioxide are contained in the gas mixture.

U.S. Pat. No. 3,651,159 discloses that a toluene solution of aluminum copper(I) chloride $CuAlCl_4$ can separate an unsaturated hydrocarbon from a gas mixture containing the same, by forming a complex with the unsaturated hydrocarbon. This process, however, has disadvantages in that, since the aluminum copper(I) chloride reacts strongly with water to irreversibly lose its complex-forming capability, the separation capacity is gradually decreased with the increase in the gas treatment amount even where the gas mixture contains as low as 1 ppm of water, and the unsaturated hydrocarbon separation apparatus is corroded due to the hydrogen chloride derived from the reaction of the aluminum copper(I) chloride with water. This process has further disadvantages in that toluene vapor must be separated from the recovered unsaturated hydrocarbon in a separate step, since the recovered unsaturated hydrocarbon released from the toluene solution of the aluminum copper(I) chloride contains the vapor of the toluene solvent, and that the process using a liquid adsorbent is disadvantageous when compared with the process using a solid adsorbent, from the viewpoints of the various process limitations. Furthermore, since the adsorbed solution contains aluminum chloride therein, a Friedel-Crafts reaction of the unsaturated hydrocarbon with toluene in the presence of the aluminum chloride catalyst occurs, as a side reaction, causing a loss of the unsaturated hydrocarbon and denation of the liquid adsorbent.

Other various processes for separating unsaturated hydrocarbons from gas mixtures have been proposed. However, until now there has been no satisfactory process in the art for separating unsaturated hydrocarbons from gas mixtures, especially by using solid adsorbents.

SUMMARY OF THE INVENTION

Accordingly, the objects of the present invention are to eliminate the above-mentioned disadvantages of the prior art and to provide a solid adsorbent which is capable of adsorbing and releasing an unsaturated hydrocarbon under relatively mild conditions.

Another object of the present invention is to provide a process for effectively separating an unsaturated hydrocarbon from a gas mixture in which the unsaturated hydrocarbon can be effectively and economically adsorbed and released.

Other objects and advantages of the present invention will be apparent from the description set forth hereinbelow.

In accordance with the present invention, there is provided a solid adsorbent for an unsaturated hydrocarbon comprising (a) (i) a copper(I) halide or oxide or (ii) a halide, carboxylate, sulfate, basic salt, oxide, or an amine complex salt of copper(II) and (b) activated carbon or graphite.

In accordance with the present invention, there is also provided a process for separating an unsaturated hydrocarbon from a gas mixture containing the same comprising the step of:

contacting the gas mixture with a solid adsorbent comprising (a) (i) a copper(I) halide or oxide or (ii) a halide, carboxylate, sulfate, basic salt, oxide, or amine complex salt of copper(II) and (b) activated carbon or graphite.

DESCRIPTION OF THE PREFERRED EMBODIMENTS

The solid adsorbent for an unsaturated hydrocarbon according to the present invention can be prepared by dissolving or suspending the component (a) in a solvent or suspension and adding the activated carbon or graphite to the resultant solution, followed by evaporating the solvent from the mixture.

Examples of the copper(I) halides usable in the present invention are copper(I) chloride, copper(I) bromide, and copper(I) iodide. These halides can be used alone or in any mixtures thereof. The copper(I) oxide can be used in the present invention instead of, or in combination with, the copper(I) halides.

Examples of the copper(II) halides usable in the present invention are copper(II) chloride, copper(II) fluoride, copper(II) bromide, and copper(II) iodide. Examples of the copper(II) carboxylates are copper(II) acetate and copper(II) formate. Examples of the basic salts are basic copper(II) carbonate, basic copper(II) acetate, and basic copper(II) phosphate. Examples of the amine salt complex are copper(II) hexamine chloride. The copper(II) oxide can be used instead of, or in combination with, the above-mentioned copper (II) compounds.

The activated carbon or graphite usable in the present invention includes any conventional activated carbon or graphite desirably having an average particle size of 50 to 20000 microns and a surface area of 300 to 3000 m$^2$/g. The activated carbon can be in the form of granulated carbon such as formed carbon, crushed carbon, and powdered carbon. The raw materials of the activated carbon are wood, coconut shell, coal, and petroleum pitch. The activated carbon can be activated either by a reagent activating method or by a gas activating method.

Examples of the solvents usable in the preparation of the present invention are water, an aqueous hydrochloric acid, formic acid, acetic acid, benzene, toluene, propionitrile, acetonitrile, aqueous ammonia, aqueous ammoniacal formic acid, or a primary or secondary alcohol having 1 to 7 carbon atoms.

A weight ratio of the activated carbon or graphite to the above-mentioned component (a) (i.e., copper(I) halide or oxide, or a halide, carboxylate, sulfate, basic salt, oxide, or amine complex salt of copper(II)) is preferably 0.5 to 60, more preferably 2.0 to 10.0. A weight ratio of the activated carbon or graphite to the component (a) of less than 0.5 tends to decrease the unsaturated hydrocarbon capacity per copper atom. Contrary to this, a weight ratio of more than 60 tends to decrease the unsaturated hydrocarbon adsorption capacity per weight. Furthermore, a weight ratio of the solvent to the component (a) is preferably 1 to 200, more preferably 3 to 30. The weight ratio of the solvent to the component (a) of less than 1 tends to decrease the unsaturated hydrocarbon capacity per copper atom. Contrary to this, the weight ratio of the solvent to the component (a) of more than 200 tends to be economically unfavorable.

As mentioned above, the present solid adsorbents can be prepared by dissolving or suspending the above-mentioned component (a) (i.e., the copper(I) salt, the copper(II) salt, copper(I) oxide, or copper(II) oxide) in the solvent at a temperature of, for example, 10° C. to 80° C., preferably 20° C. to 30° C., for 1 minute to 10 hours, preferably 1 hour to 3 hours, while stirring, under an inert atmosphere of, for example, nitrogen, argon, helium, or air, and then removing the solvent by, for example, reduced distillation (e.g., at a temperature of 10° C. to 500° C., preferably 80° C. to 250° C., under an absolute pressure of $10^{-6}$ mm Hg to $10^2$ mm Hg, preferably $10^{-2}$ mm Hg to 10 mm Hg).

The unsaturated hydrocarbons which can be separately adsorbed by the present adsorbents are monoolefins having 2 to 15 carbon atoms (e.g., ethylene, propylene, 1-butene, 2-butene, 1-pentene, 2-pentene, 1-hexene, 2-hexene, cyclopentene, and cyclohexene) and dienes (e.g., butadiene, chloroprene, isoprene, pentadiene, hexadiene, cyclopentadiene, and cyclohexadiene).

As illustrated in the examples given hereinbelow, the adsorbent of the present invention can effectively adsorb an unsaturated hydrocarbon contained in a gas mixture by contacting the gas mixture with the present adsorbent at a temperature of −40° C. to 90° C., preferably 0° C. to 40° C., under normal pressure (e.g., 1 atm). The unsaturated hydrocarbon adsorption can be also carried out under an elevated pressure. In this case, the adsorption can be carried out at a temperature higher than 90° C.

The adsorbed unsaturated hydrocarbon is readily released or desorbed by heating the adsorbents at a temperature of 40° C. to 250° C., preferably 60° C. to 180° C. The desorption of the unsaturated hydrocarbon can be also readily carried out by evacuating the system containing the adsorbent or decreasing a partial pressure of the unsaturated hydrocarbon in the system containing the adsorbent.

The solid adsorbents of the present invention are inert and stable against the water possibly contained in the gas mixtures to be treated and, therefore, the desired unsaturated hydrocarbon can be directly separated from the gas mixture containing water (e.g., approximately 40,000 ppm by volume at 30° C. or less) without causing a substantial decrease in the adsorbing capacity of the unsaturated hydrocarbon after repeated use, as illustrated in the Examples hereinbelow. Furthermore, the present solid adsorbents do not catalyze a Friedel-Crafts reaction of the unsaturated hydrocarbons.

The solid adsorbents of the present invention can be packed in a packed column, a packed tower, and a fluidized bed to adsorb and desorb unsaturated hydrocarbons.

EXAMPLES

The present invention will now be further illustrated by, but is by no means limited to, the following examples.

Example 1

The following chemicals and gases were used in this Example.

Copper(I) chloride: special grade chemical copper(I) chloride, manufactured by Komune Kagaku Yakuhin Kabushiki Kaisha (Japan).

Hydrochloric acid: first grade chemical hydrochloric acid (manufactured by Takahashi Tokichi Shoten (Japan)) diluted to 3N HCl by purified water (manufactured by Yugen Kaisha Tokyo Yakuhin Kougyosho (Japan)).

Activated carbon: BAC, G-70R, Lot No. 810 117 (manufactured by Kureha Kagaku Kogyo Kabushiki Kaisha, derived from steam activation of petroleum pitch raw material) was used after heating at 180° C. for 24 hours and storing it under a dry nitrogen atmosphere.

Ethylene gas: a bomb gas (manufactured by Takachiho Kagaku Kabushiki Kaisha (Japan)) was used after adjusting the water content to 0.6 mol% (i.e., 6000 ppm).

Nitrogen: a bomb gas (manufactured by Kabushiki Kaisha Suzuki Shokan (Japan)), was dried and purified by passing the gas through a column packed with molecular sieve 3A (Nikka Seiko Kabushiki Kaisha, Japan) just before use.

A 1.5 g (15.2 mmol) amount of copper(I) chloride was charged into a 100 ml two-necked eggplant-type flask and 15 ml of 3N hydrochloric acid was added thereto under a dry nitrogen atmosphere. The resultant mixture was allowed to stand at 20° C. for 1 hour, while stirring with a magnetic stirrer. A 10 g amount of the activated carbon was then charged into the flask under a nitrogen atmosphere and the mixture was stirred for one hour. The flask was evacuated to 6 mm Hg at 100° C. to thoroughly remove water and hydrogen chloride.

Thus, a solid adsorbent in the form of black particles was obtained.

The adsorbent was charged into a 100 ml two-necked, eggplant-type flask and the flask was connected to a vessel containing 1.5 liters of a gas mixture of ethylene and nitrogen at 1 atm (partial pressure: ethylene 0.9 atm, $N_2$ 0.1 atm). Thus, ethylene was adsorbed onto the adsorbent at 20° C., while the adsorbent was stirred with a magnetic stirrer. The gas mixture was circulated through the flask with a BA-106T air pump (manufactured by Kabushiki Kaisha Iwaki, Japan) during the initial 10 min. adsorption period, while the adsorbent was stirred with a magnetic stirrer. The amount of ethylene adsorbed onto the adsorbent was determined at 20° C. according to the gas burette method.

The ethylene was rapidly adsorbed onto the adsorbent. That is, 3.4 mmol of ethylene was adsorbed after 10 minutes and 4.5 mmol of ethylene was adsorbed after 60 minutes.

The adsorbent was then heated at 100° C. under 1 atm to release the ethylene therefrom. The ethylene was rapidly desorbed. The amount of the ethylene desorbed from the adsorbent was determined according to a gas burette method. As a result, 4.5 mmol of ethylene was released after 10 minutes. The released gas was found by a gas chromatograph analysis to be ethylene and no other component was detected in the released gas.

The ethylene was again adsorbed onto the adsorbent contained in the flask by connecting the flask to a vessel containing 1.5 liters of a gas mixture of ethylene and nitrogen at 1 atm (partial pressure: ethylene 0.9 atm, $N_2$ 0.1 atm), while the adsorbent was stirred with a magnetic stirrer.

The ethylene was rapidly adsorbed onto the adsorbent. That is, 3.4 mmol of ethylene was adsorbed after 60 minutes.

The adsorbent was then heated at 100° C. under 1 atm to rapidly release the adsorbed ethylene. The amount of the ethylene desorbed from the adsorbent was determined according to a gas burette method. The released amount of the ethylene was 3.4 mmol after 10 minutes.

No substantial change of the adsorption rate and adsorption amount of ethylene was observed by the further repeated operations.

Example 2

The chemicals, gases, and adsorbent used in Example 1 were used in this Example.

The adsorbent was charged into a 100 ml two-necked, eggplant-type flask and the flask was connected to a vessel containing 1.5 liters of a gas mixture of ethylene and nitrogen at 1 atm (partial pressure: ethylene 0.9 atm, $N_2$ 0.1 atm). Thus, ethylene was adsorbed onto the adsorbent at 20° C., while the adsorbent was stirred with a magnetic stirrer. The gas mixture was circulated through the flask with a BA-106T air pump (manufactured by Kabushiki Kaisha Iwaki, Japan) during the initial 10 minute adsorption period, while the adsorbent was stirred with a magnetic stirrer. The amount of ethylene adsorbed onto the adsorbent was determined at 20° C. according to the gas burette method.

The ethylene was rapidly adsorbed onto the adsorbent. That is, 3.4 mmol of ethylene was adsorbed after 10 minutes and 4.5 mmol of ethylene was adsorbed after 60 minutes.

The ethylene adsorbed was desorbed at 20° C. by evacuating the flask to 0.4 mm Hg for 10 minutes.

The ethylene was again adsorbed onto the adsorbent contained in the flask by connecting the flask to a vessel containing 1.5 liters of a gas mixture of ethylene and nitrogen at 1 atm (partial pressure: ethylene 0.9 atm, $N_2$ 0.1 atm), while the adsorbent was stirred with a magnetic stirrer.

The ethylene was rapidly adsorbed onto the adsorbent. That is, 3.7 mmol of ethylene was adsorbed after 60 minutes.

No substantial change of the adsorption rate and adsorption amount of ethylene was observed by the further repeated operations.

Example 3

The chemicals, gases, and adsorbent used in Example 1 were used in this Example, except that propylene gas generated from special grade chemical propylene (50% xylene solution) (manufactured by Tokyo Kasei Kogyo Kabushiki Kaisha (Japan)) was used after being purified by passing it through a packed column of activated carbon.

The adsorbent was charged into a 100 ml two-necked, eggplant-type flask and the flask was connected to a vessel containing 1.5 liters of a gas mixture of propylene and nitrogen at 1 atm (partial pressure: propylene 0.9 atm, $N_2$ 0.1 atm). Thus, propylene was adsorbed onto the adsorbent at 20° C., while the adsorbent was stirred with a magnetic stirrer. The gas mixture was circulated through the flask with a BA-106T air pump (manufactured by Kabushiki Kaisha Iwaki, Japan) during the initial 10 minute adsorption period, while the adsorbent was stirred with a magnetic stirrer. The amount of propylene adsorbed onto the adsorbent was determined at 20° C. according to the gas burette method.

The propylene was rapidly adsorbed onto the adsorbent. That is, 4.4 mmol of propylene was adsorbed after 10 minutes and 5.7 mmol of propylene was adsorbed after 60 minutes. The propylene adsorbed was desorbed at 20° C. by evacuating the flask to 0.4 mm Hg for 10 minutes.

The propylene was again adsorbed onto the adsorbent contained in the flask by connecting the flask to a vessel containing 1.5 liters of a gas mixture of propylene and nitrogen at 1 atm (partial pressure: propylene 0.9 atm, $N_2$ 0.1 atm), while the adsorbent was stirred with a magnetic stirrer.

The propylene was rapidly adsorbed onto the adsorbent. That is, 3.3 mmol of propylene was adsorbed after 60 minutes.

No substantial change of the adsorption rate and adsorption amount of propylene was observed by the further repeated operations.

Example 4

The chemicals and gases used in Example 1 were used, except that special grade chemical copper(II) chloride dihydrate (manufactured by Komune Kagaku Yakuhin Kabushiki Kaisha (Japan)) was used instead of the copper(I) chloride and purified water (manufactured by Yugen Kaisha Tokyo Yakuhin Kogyosho (Japan)) was used instead of the 3N hydrochloric acid.

A 2.6 g (15.0 mmol) amount of copper(II) chloride dihydrate was charged into a 100 ml two-necked eggplant-type flask and 15 ml of the purified water was added thereto under a dry nitrogen atmosphere. The resultant mixture was allowed to stand at 20° C. for 1 hour, while stirring with a magnetic stirrer. A 10 g amount of the activated carbon was then charged into the flask under a nitrogen atmosphere and the mixture was stirred for one hour. The flask was evacuated to 6 mm Hg at 180° C. to thoroughly remove water. Thus, a solid adsorbent in the form of block particles was obtained.

The adsorbent was charged into a 100 ml two-necked, eggplant-type flask and the flask was connected to a vessel containing 1.5 liters of a gas mixture of ethylene and nitrogen at 1 atm (partial pressure: ethylene 0.9 atm, $N_2$ 0.1 atm). Thus, ethylene was adsorbed onto the adsorbent at 20° C., while the adsorbent was stirred with a magnetic stirrer. The gas mixture was circulated through the flask with a BA-106T air pump (manufactured by Kabushiki Kaisha Iwaki, Japan) during the initial 10 minute adsorption period, while the adsorbent was stirred with a magnetic stirrer. The amount of ethylene adsorbed onto the adsorbent was determined at 20° C. according to the gas burette method.

The ethylene was rapidly adsorbed onto the adsorbent. That is, 3.3 mmol of ethylene was adsorbed after 10 minutes and 4.2 mmol of ethylene was adsorbed after 60 minutes.

The ethylene adsorbed was desorbed at 20° C. by evacuating the flask to 0.4 mm Hg for 10 minutes with a vacuum pump.

The ethylene was again adsorbed onto the adsorbent contained in the flask by connecting the flask to a vessel containing 1.5 liters of a gas mixture of ethylene and nitrogen at 1 atm (partial pressure: ethylene 0.9 atm, $N_2$ 0.1 atm), while the adsorbent was stirred with a magnetic stirrer.

The ethylene was rapidly adsorbed onto the adsorbent. That is, 4.0 mmol of ethylene was adsorbed after 60 minutes.

No substantial change of the adsorption rate and adsorption amount of ethylene was observed by the further repeated operations.

Example 5

The chemicals and gases used in Example 1 were used, except that special grade chemical copper(I) bromide (manufactured by Yoneyama Yakuhin Kogyo Kabushiki Kaisha (Japan)) was used instead of the copper(I) chloride and 28% aqueous ammonia (manufactured by Yugen Kaisha Takahashi Tokichi Shoten (Japan)) was used instead of the 3N hydrochloric acid.

A 2.2 g (15.0 mmol) amount of copper(I) bromide was charged into a 100 ml two-necked eggplant-type flask and 15 ml of the aqueous ammonia was added thereto under a dry nitrogen atmosphere. The resultant mixture was allowed to stand at 20° C. for 1 hour, while stirring with a magnetic stirrer. A 10 g amount of the activated carbon was then charged into the flask under a nitrogen atmosphere and the mixture was stirred for one hour. The flask was evacuated to 6 mm Hg at 100° C. to thoroughly remove the water and ammonia. Thus, a solid adsorbent in the form of black particles was obtained.

The adsorbent was charged into a 100 ml two-necked, eggplant-type flask and the flask was connected to a vessel containing 1.5 liters of a gas mixture of ethylene and nitrogen at 1 atm (partial pressure: ethylene 0.9 atm, $N_2$ 0.1 atm). Thus, ethylene was adsorbed onto the adsorbent at 20° C., while the adsorbent was stirred with a magnetic stirrer. The gas mixture was circulated through the flask with a BA-106T air pump (manufactured by Kabushiki Kaisha Iwaki, Japan) during the initial 10 minute adsorption period, while the adsorbent was stirred with a magnetic stirrer. The amount of ethylene adsorbed onto the adsorbent was determined at 20° C. according to the gas burette method.

The ethylene was rapidly adsorbed onto the adsorbent. That is, 2.3 mmol of ethylene was adsorbed after 10 minutes and 3.3 mmol of ethylene was adsorbed after 60 minutes.

Example 6

The chemicals and gases used in Example 1 were used, except that anhydrous copper(II) sulfate (manufactured by Yoneyama Yakuhin Kogyo Kabushiki Kaisha (Japan)) was used instead of the copper(I) chloride and 35% hydrochloric acid (manufactured by Yugen Kaisha Takahashi Tokichi Shoten (Japan)) was used instead of the 3N hydrochloric acid.

A 2.4 g (15 mmol) amount of anhydrous copper(II) sulfate was charged into a 100 ml two-necked eggplant-type flask and 15 ml of the 35% hydrochloric acid was added thereto under a dry nitrogen atmosphere. The resultant mixture was allowed to stand at 20° C. for 1 hour, while stirring with a magnetic stirrer. A 10 g amount of the activated carbon was then charged into the flask under a nitrogen atmosphere and the mixture was stirred for one hour. The flask was evacuated to 6 mm Hg at 100° C. to thoroughly remove water and hydrogen chloride. Thus, a solid adsorbent in the form of black particles was obtained.

The adsorbent was charged into a 100 ml two-necked, eggplant-type flask and the flask was connected to a vessel containing 1.5 liters of a gas mixture of ethylene and nitrogen at 1 atm (partial pressure: ethylene 0.9 atm, $N_2$ 0.1 atm). Thus, ethylene was adsorbed onto the adsorbent at 20° C., while the adsorbent was stirred with a magnetic stirrer. The gas mixture was circulated through the flask with a BA-106T air pump (manufactured by Kabushiki Kaisha Iwaki, Japan) during the initial 10 minute adsorption period, while the adsorbent was stirred with a magnetic stirrer. The amount of ethylene adsorbed onto the adsorbent was determined at 20° C. according to the gas burette method.

The ethylene was rapidly adsorbed onto the adsorbent. That is, 2.0 mmol of ethylene was adsorbed after 10 minutes and 3.2 mmol of ethylene was adsorbed after 60 minutes.

Comparative Example 1

The activated carbon, ethylene, and nitrogen used in Example 1 were used.

A 10 g amount of the activated carbon was charged into a 100 ml two-necked, eggplant-type flask and the flask was connected to a vessel containing 1.5 liters of a gas mixture of ethylene and nitrogen at 1 atm (partial pressure: ethylene 0.9 atm, $N_2$ 0.1 atm). Thus, ethylene was adsorbed onto the adsorbent at 20° C., while the adsorbent was stirred with a magnetic stirrer. The gas mixture was circulated through the flask with a BA-106T air pump (manufactured by Kabushiki Kaisha Iwaki, Japan) during the initial 10 minute adsorption period, while the adsorbent was stirred with a magnetic stirrer. The amount of ethylene adsorbed onto the adsorbent was determined at 20° C. according to the gas burette method.

The ethylene was adsorbed in an amount of 0.12 mmol after 10 minutes and 1.2 mmol after 60 minutes. Thus, the adsorption amount of an unsaturated hydrocarbon onto the activated carbon (not containing the copper compound) is remarkably smaller than that of the present solid adsorbent.

Example 7

The chemicals and gases used in Example 1, except that copper(I) oxide (manufactured by Yoneyama Yakuhin Kogyo Kabushiki Kaisha (Japan)) was used instead of the copper(I) chloride.

A 2.1 g (15.0 mmol) amount of copper(I) oxide was charged into a 100 ml two-necked eggplant-type flask and 15 ml of 2N hydrochloric acid was added thereto under a dry nitrogen atmosphere. The resultant mixture was allowed to stand at 20° C. for 1 hour, while stirring with a magnetic stirrer. A 10 g amount of the activated carbon was then charged into the flask under a nitrogen atmosphere and the mixture was stirred for one hour. The flask was evacuated to 6 mm Hg at 100° C. to thoroughly remove the water and hydrogen chloride. Thus, a solid adsorbent in the form of black particles was obtained.

The ethylene adsorption amounts were determined in the same manner as in Example 1.

As a result, 5.3 mmol of ethylene was adsorbed onto the adsorbent after 3 minutes and 7.2 mmol of ethylene after 60 minutes.

Example 8

The chemicals, gases, and adsorbent used in Example 1 were used, except that propylene gas generated from special grade chemical propylene (50% xylene solution) (manufactured by Tokyo Kasei Kabushiki Kaisha (Japan)) was used after being purified by it passing through a packed column of activated carbon.

The adsorbent was charged into a 100 ml two-necked, eggplant-type flask and the flask was connected to a vessel containing 1.5 liters of a gas mixture of propylene and nitrogen at 1 atm (partial pressure: propylene 0.9 atm, $N_2$ 0.1 atm). Thus, propylene was adsorbed onto the adsorbent at 20° C., while the adsorbent was stirred with a magnetic stirrer. The gas mixture was circulated through the flask with a BA-106T air pump (manufactured by Kabushiki Kaisha Iwaki, Japan) during the initial 10 minute adsorption period, while the adsorbent was stirred with a magnetic stirrer. The amount of propylene adsorbed onto the adsorbent was determined at 20° C. according to the gas burette method.

The propylene was rapidly adsorbed onto the adsorbent. That is, 4.4 mmol of propylene was adsorbed after 10 minutes and 5.7 mmol of propylene was adsorbed after 60 minutes.

The adsorbent was then heated at 100° C. under 1 atm to rapidly release the adsorbed propylene. The released amount of the propylene was 5.6 mmol after 5 minutes.

Example 9

The chemicals and gases used in Example 1 were used, except that special grade chemical copper(I) bromide (manufactured by Yonegama Yakuhin Kogyo Kabushiki Kaisha (Japan)) was used instead of the copper(I) chloride and special grade chemical methanol (manufactured by Nakarai Kagaku Yakuhin Kabushiki Kaisha (Japan)) was used instead of the 3N hydrochloric acid.

A 2.1 g (15.0 mmol) amount of copper(I) bromide was charged into a 100 ml two-necked eggplant-type flask and 15 ml of the methanol was added thereto under a dry nitrogen atmosphere. The resultant mixture was allowed to stand at 20° C. for 1 hour, while stirring with a magnetic stirrer. A 10 g amount of the activated carbon was then charged into the flask under a nitrogen atmosphere and the mixture was stirred for one hour. The flask was evacuated to 6 mm Hg at 100° C. to thoroughly remove the methanol. Thus, a solid adsorbent in the form of black particles was obtained.

The ethylene adsorption amount was determined in the same manner as in Example 1.

As a result, 1.8 mmol of ethylene was adsorbed onto the adsorbent after 3 minutes, and 2.6 mmol of ethylene after 60 minutes.

The ethylene adsorbed adsorbent thus obtained was heated at 120° C. under 1 atm to rapidly release the ethylene. The released ethylene amount was 2.6 mmol after 10 minutes. The released gas was analyzed by a gas chromatography (Porapak Q column having a length of 2 m at a column temperature of 60° C.) to find that the release gas contained only ethylene and that no other component was detected.

Example 10

The chemicals and gases used in Example 1 were used, except that special grade chemical acetonitrile (manufactured by Tokyo Kasei Yakuhin Kogyo Kabushiki Kaisha) was used instead of the 3N hydrochloric acid.

A 1.5 g (15.2 mmol) amount of copper(I) chloride was charged into a 100 ml two-necked eggplant-type flask and 15 ml of acetonitrile was added thereto under a dry nitrogen atmosphere. The resultant mixture was allowed to stand at 20° C. for 1 hour, while stirring with a magnetic stirrer. A 10 g amount of the activated carbon was then charged into the flask under a nitrogen atmosphere and the mixture was stirred for one hour. The flask was evacuated to 6 mm Hg at 100° C. to thoroughly remove acetonitrile. Thus, a solid adsorbent in the form of black particles was obtained.

The ethylene adsorption amount was determined in the same manner as in Example 1.

The ethylene was rapidly adsorbed onto the adsorbent. That is, 2.2 mmol of ethylene was adsorbed after 3 minutes, and then, 3.5 mmol of ethylene, the approximate equilibrium adsorption amount, was adsorbed after 60 minutes.

Example 11

The chemicals and gases used in Example 1 were used, except that activated carbon SGW-079 (manufactured by Takeda Yakuhin Kogyo Kabushiki Kaisha, granule type "Shirasagi $C_2$ ×4/6−3, derived from coconut shell carbon, steam activated carbon) was used instead of the activated carbon BAC, G70R.

A 1.5 g (15.2 mmol) amount of copper(I) chloride was charged into a 100 ml two-necked eggplant-type flask and 15 ml of 3N hydrochloric acid was added thereto under a dry nitrogen atmosphere. The resultant mixture was allowed to stand at 20° C. for 2 hours, while stirring with a magnetic stirrer. A 10 g amount of the activated carbon SGW-079 was then charged into the flask under a nitrogen atmosphere and the mixture was stirred for one hour. The flask was evacuated to 6 mm Hg at 120° C. to thoroughly remove water and hydrogen chloride. Thus, a solid adsorbent in the form of black particles was obtained.

The ethylene adsorption amounts of the adsorbent were determined in the same manner as in Example 1.

As a result, 3.3 mmol of ethylene was adsorbed onto the adsorbent after 3 minutes and 4.2 mmol after 60 minutes.

We claim:

1. A process for recovering an unsaturated hydrocarbon from a gas mixture containing the same comprising the steps of:
   (1) contacting the gas mixture with solid adsorbent, said solid adsorbent comprising:
   (a) a cooper (I) halide or oxide and
   (b) activated carbon or graphite,
   and being prepared by dissolving or suspending a component (a) in an aqueous hydrochloric acid and adding the activated carbon or graphite to a resultant solution or suspension, followed by evaporating a solvent from a mixture; and then
   (2)
   (i) heating the solid adsorbent
   (ii) evacuating a system containing the solid adsorbent, or
   (iii) decreasing a partial pressure of an unsaturated hydrocarbon in the system containing the solid adsorbent whereby the adsorbed unsaturated hydrocarbon is released.

2. A process as claimed in claim 1, wherein the unsaturated hydrocarbon is a monoolefin having 2 to 5 carbon atoms, a polyolefin, or a diene.

3. A process as claimed in claim 1, wherein the unsaturated hydrocarbon is ethylene.

4. A process as claimed in claim 1, wherein the gas mixture is placed in contact with the solid adsorbent at a temperature of $-40°$ C. to $90°$ C. under normal pressures.

5. A solid adsorbent for an unsaturated hydrocarbon comprising:
   (a) a cooper (I) halide or oxide and
   (b) activated carbon or graphite,
   said solid adsorbent being prepared by dissolving or suspending a component (a) in an aqueous hydrochloric acid and adding the activated carbon or graphite to a resultant solution or suspension, followed by evaporating a solvent from a mixture.

6. A solid adsorbent as claimed in claim 5, wherein a weight ratio of a component (b) to the component (a) is 0.5 to 60.0.

7. A solid adsorbent as claimed in claim 5, wherein the copper (I) halide is copper (I) chloride.

* * * * *